US012685623B2

(12) United States Patent
Brandao Silva et al.

(10) Patent No.: US 12,685,623 B2
(45) Date of Patent: Jul. 21, 2026

(54) CLEANING AND/OR TREATMENT UNIT FOR AN ORAL CARE DEVICE

(71) Applicant: KONINKLIJKE PHILIPS N.V., Eindhoven (NL)

(72) Inventors: Priscilla Brandao Silva, Eindhoven (NL); Lutz Christian Gerhardt, Eindhoven (NL); Mark Thomas Johnson, Arendonk (BE); Bart Gottenbos, Budel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 308 days.

(21) Appl. No.: 18/269,142

(22) PCT Filed: Nov. 19, 2021

(86) PCT No.: PCT/EP2021/082359
§ 371 (c)(1),
(2) Date: Jun. 22, 2023

(87) PCT Pub. No.: WO2022/135805
PCT Pub. Date: Jun. 30, 2022

(65) Prior Publication Data
US 2024/0130841 A1        Apr. 25, 2024
US 2024/0225802 A9        Jul. 11, 2024

(30) Foreign Application Priority Data
Dec. 22, 2020     (EP) ..................................... 20216414

(51) Int. Cl.
*A61C 17/22*        (2006.01)
*A61N 1/05*        (2006.01)

(52) U.S. Cl.
CPC ............ *A61C 17/22* (2013.01); *A61N 1/0548* (2013.01)

(58) Field of Classification Search
CPC .... A46B 15/0022; A61C 17/22; A61N 1/0548
See application file for complete search history.

(56) References Cited

U.S. PATENT DOCUMENTS 9,585,687 B2     3/2017     Tenenbaum et al.
10,201,701 B2     2/2019     Levi
(Continued)

FOREIGN PATENT DOCUMENTS

GB             2117230 A     10/1983
WO         2013042307 A1     3/2013
(Continued)

OTHER PUBLICATIONS

International Search Report and Written Opinion Dated Jan. 24, 2022 for International Application No. PCT/EP2021/082359 Filed Nov. 19, 2021.
(Continued)

*Primary Examiner* — Shay Karls

(57)        ABSTRACT

A shielding barrier (32) is carried by one or more electrodes (22) of a cleaning and/or treatment unit (12) for an oral care device, and arranged for interposing contact of an exposed conductive portion (25) of the electrodes (22) by other components or external objects. The shielding barrier is arranged such that the exposed conductive portion is still at least partially open to the environment surrounding the electrodes (22).

11 Claims, 3 Drawing Sheets

(56)     References Cited

U.S. PATENT DOCUMENTS

| | | | |
|---|---|---|---|
| 2008/0091192 | A1 | 4/2008 | Paul et al. |
| 2008/0280248 | A1 | 11/2008 | Pitts et al. |
| 2011/0232014 | A1 | 9/2011 | Uchida |
| 2011/0289699 | A1 | 12/2011 | Schaefer et al. |
| 2012/0233791 | A1* | 9/2012 | Uchida ................ A46D 1/0207 |
| | | | 15/167.1 |
| 2019/0380482 | A1 | 12/2019 | Edwards et al. |
| 2021/0330068 | A1* | 10/2021 | Levi ..................... A46B 13/008 |

FOREIGN PATENT DOCUMENTS

| | | | |
|---|---|---|---|
| WO | 2013084863 | A1 | 6/2013 |
| WO | 2017216606 | A1 | 12/2017 |
| WO | 2021239549 | A1 | 12/2021 |
| WO | 2021239553 | A1 | 12/2021 |
| WO | 2021239554 | A1 | 12/2021 |
| WO | 2021239556 | A1 | 12/2021 |

OTHER PUBLICATIONS

ToothWave—Way Beyond Brushing. Silk'n Australia Youtube Video https://www.youtube.com/watch?v=orTsVwZLC10 Mar. 18, 2019.

* cited by examiner

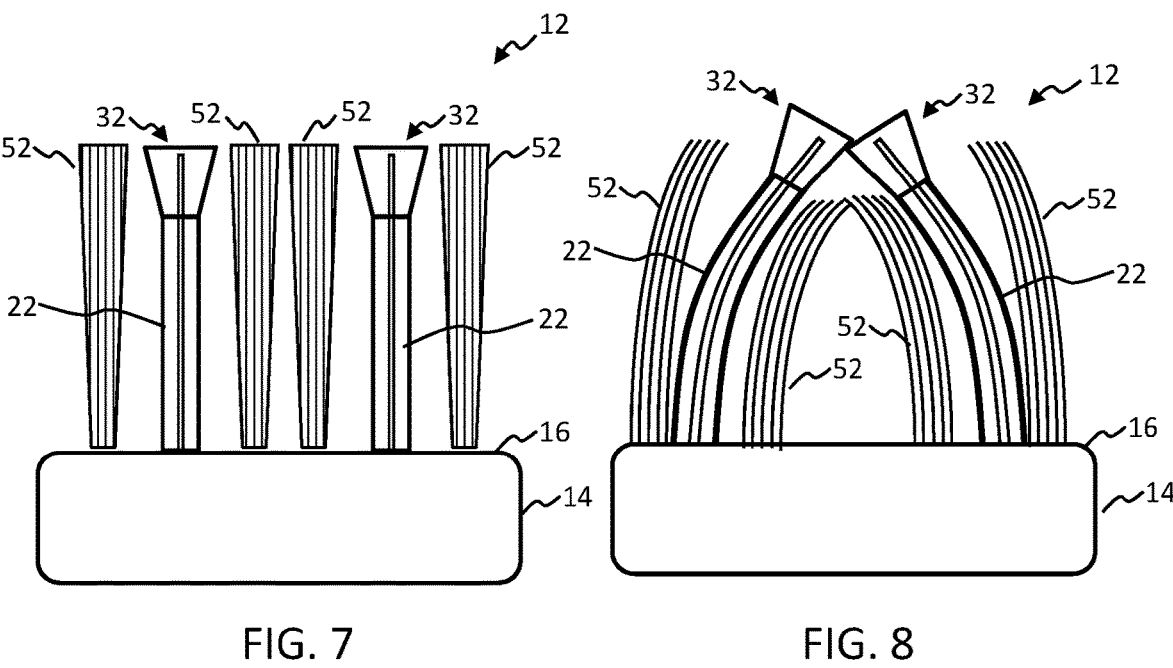
FIG. 7                    FIG. 8
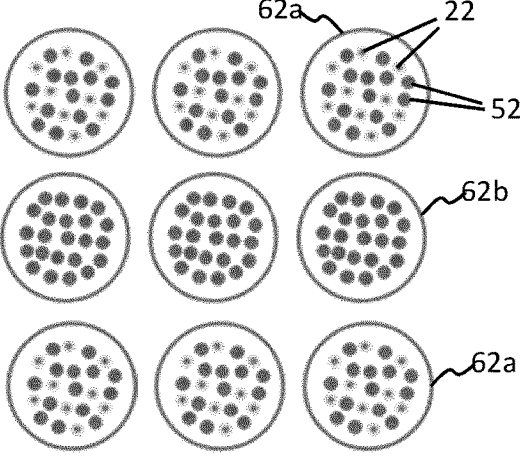
FIG. 9

CLEANING AND/OR TREATMENT UNIT FOR AN ORAL CARE DEVICE

This application is the U.S. National Phase application under 35 U.S.C. § 371 of International Application No. PCT/EP2021/082359, filed on Nov. 19, 2021, which claims the benefit of EP Application Serial No. 20216414.1, filed Dec. 22, 2020. These applications are hereby incorporated by reference herein.

FIELD OF THE INVENTION

The present invention relates to a cleaning and/or treatment unit for an oral care device, in particular a cleaning and/or treatment unit having electrodes for generating electromagnetic emissions.

BACKGROUND OF THE INVENTION

US 2012/233791 A1 discloses a brush body for selectively applying localized currents, for oral care, to oral interstices such as periodontal pockets. The brush body has a plurality of bristle bundles in a brush head. A bristle bundle contains a bristle having a core and a sheath. The core comprises a conductive member and the sheath comprises an insulating member that covers that core. At the tip portion of the bristle, the core protrudes further than the sheath and acts as an electrode.

US 2019/380482 A1 discloses an attachment for an oral care device. The attachment comprises a treatment element. The treatment element includes a first electrode and a second electrode, and the electrodes are arranged such that, when the first and second electrodes are placed in contact with tissue within an oral cavity of a user, an applied current is able to flow from the first electrode to the second electrode, via the tissue.

WO 2017/216606 A1 discloses an oral cleaning device that includes a head portion that supports cleaning elements, a handle portion extending from the head portion, an RF generator disposed in the handle portion, connected to electrodes located on the head portion, and additionally or alternatively, a microcurrent source disposed in the handle portion, connected to a conductive surface located on the handle and to one of the electrodes located on the head portion, and a non-conductive barrier located on the head portion that separates the electrodes from each other.

A recent development in the oral healthcare field are oral care devices that generate radio frequency (RF) electromagnetic fields or emissions for an oral cleaning and/or treatment function.

Radio frequency (RF) electromagnetic emissions can be used to provide a cleaning and/or treatment function in the oral cavity. In particular, when the RF field interacts with surfaces of the teeth and gums, it may change surface properties of surfaces in the mouth which may soften surface deposits such as plaque or dental calculus, allowing them to be removed more easily. The RF emissions may also provide a treatment function through inducing a mild heating action in tissue.

In some known examples, relatively stiff electrodes, outwardly extending from a surface of a cleaning and/or treatment unit, are used for generating the RF emissions. However, these reduce the available surface area for cleaning filaments such as bristles, thus reducing mechanical cleaning efficiency. As an alternative, flexible emitters can be provided, with a similar size and bending profile as the cleaning filaments. They may be integrated into the cleaning filament field without significant loss of surface area. They may in some cases provide a dual function of mechanical cleaning and RF field generation.

However, one difficulty with such arrangements is that the flexible emitters are at high risk of short-circuits due to contact between electrically exposed portions of neighboring emitters. This can occur due to e.g. mechanical deformation, bending, splaying and abrasive wear of emitters. The short-circuiting causes damage to the functionality of the emitters. The short-circuits also pose a safety hazard to users since short circuits happening in the mouth can potentially lead to harmful burns.

Improvements in the field of cleaning and/or treatment units for oral care devices, capable of overcoming the abovementioned problems, would be of value.

SUMMARY OF THE INVENTION

The invention is defined by the independent claims. The dependent claims define advantageous embodiments.

According to examples of the invention, there is provided a cleaning and/or treatment unit for an oral care device comprising: a support body; a plurality of electrodes outwardly extending from a surface of the support body, the electrodes each comprising a conductive element having at least a portion which is exposed; and at least one barrier comprising one or more walls arranged to at least partially shield the exposed portion against physical contact, for example against contact by at least one other of the plurality of electrodes.

The barrier may comprise a physical barrier element. The barrier may be carried by the at least one electrode which it shields. The barrier may be an electrically insulating barrier element.

The barrier is arranged to interpose physical contact of the exposed portion of the conductive element, e.g. by other components of the cleaning and/or treatment unit or by external objects. External objects might include for example amalgam fillings, or metallic components in dental aligners.

The one or more walls of the barrier may be spaced from the exposed portion of the conductive element. In some examples, there is no contact between the barrier and the exposed portion of the conductive element, i.e. there is an air gap between the exposed portion of the conductive element and the barrier. In further examples, there may be a solid contact between at least a portion of the wall(s) of the barrier and the conductive element. Herein, the notion 'wall' is not limited to something solid, but also includes the possibility of having a flexible barrier which could flex/bend with the electrode. But what matters is that the wall is arranged (e.g. shaped) to prevent the exposed portion of an electrode from being physical contacted.

The barrier may comprise a unitary (monolithic) physical structure, or it may comprise a multi-material structure.

As the unit is moved around across surfaces in the mouth, or electrodes degrade, electrodes may bend toward one another, which leads to a risk of short-circuiting due to contact. Short circuiting is a safety hazard due to the excess heat generated, and also due to high intensity RF fields generated if two or more of the electrodes of the plurality of electrodes are close together. Embodiments of the invention provide an additional barrier associated with, e.g. coupled to or extending from, at least a subset of the electrodes and arranged to block or intercept physical contact of an exposed portion of the electrode conductive element by electrodes, or by other physical components of the cleaning and/or treatment unit. This thereby helps to prevent possible short-circuiting which may occur as a result of contact between electrodes of different polarities.

Thus, the structural design of the electrodes is configured so as to prevent physical contact between exposed conductive element portions of different electrodes carried by the cleaning and/or treatment unit.

The barrier is preferably electrically insulating. Electrically insulating means at least more electrically insulating than the material of the conductive element.

'Exposed' in this context means that the conductive element is open to, or in direction fluid communication with, the environment surrounding the cleaning and/or treatment unit, e.g. the environment of the oral cavity when received therein.

The exposed portion of the conductive element is preferably a distal or tip portion, extending from a terminal distal point of the conductive element to a more proximal point. Proximal in this disclosure means closer to a surface of the oral cleaning and/or treatment unit, and distal means further from a surface of the oral cleaning and/or treatment unit.

The barrier is preferably arranged to interpose contact from directions lateral with respect to the electrode, where lateral means a direction perpendicular to a length dimension of the electrode.

In some examples, the plurality of electrodes may comprise a plurality of pairs of electrodes and wherein, in operation, the electrodes of a given pair are driven with different (e.g. opposite polarity) voltages. This means that there is a potential difference between the electrodes of such a pair, which generates an electric field between the electrodes of the pair.

The barrier of at least one of the electrodes may be arranged to interpose physical contact of the exposed portion of the conductive element by another electrode on the surface bending toward the exposed portion, for example a neighboring electrode.

The barrier element may for example be arranged to interpose contact of the exposed portions of the electrodes of each pair of electrodes upon bending of the electrodes toward one another.

The walls of the barrier may be arranged spaced from the exposed portion of the conductive element.

The cleaning and/or treatment unit may in some examples be an integral portion of an oral care device (e.g. an integral mouthpiece section of a brushing mouthpiece device), or may be a removable attachment for an oral care device, e.g. a cleaning head for a toothbrush, or a removable mouthpiece section of a mouthpiece device.

Each of the electrodes may be flexible. In particular, each may be flexible in a lateral direction, the lateral direction being perpendicular to a length of the electrode, the length extending from a proximal end of the member, connected to the cleaning unit surface, and a distal end.

In accordance with one or more embodiments, the cleaning and/or treatment unit may further comprise a plurality of cleaning elements outwardly extending from the surface of the support body for mechanically engaging with surfaces in an oral cavity of a user for a cleaning function. The cleaning elements for example comprise cleaning filaments such as bristles. The electrodes may be located within the bristle field.

The plurality of cleaning elements may comprise at least one spatial group of cleaning elements, the spatial group covering an area of the support body surface, and wherein at least a subset of the plurality of electrodes outwardly extends from locations on the support body surface within that area. The spatial group for example forms a tuft of cleaning elements.

The electrodes may extend to the same length from the surface as the cleaning elements.

In some cases, at least two electrodes may be located within the same tuft. This makes short-circuiting more likely. The electrodes may for example be a pair of electrodes driven with differing voltages in operation. The barrier is thus of particular utility in such circumstances.

The one or more walls of the barrier may each be arranged facing opposite at least a portion of an outer surface of the exposed portion of the conductive element. They may be spaced from the outer surface of the exposed portion.

Since the walls are arranged facing the outer surface(s) of the exposed portion of the conductive element, and in opposition to the outer surface(s), the walls form a physical shield against physical contact of the exposed portion by external bodies approaching from a direction of the reverse sides of the walls. The walls are for example axially aligned with the exposed surfaces of the exposed portion of the conductive element, where the axial direction is defined by a length dimension of the electrode.

In some embodiments, the barrier may be an annular element having an annular wall which annularly surrounds the exposed portion of the conductive element. There may be a radial spacing between the annular wall and the exposed portion of the conductive element. For example, the annular wall may coaxially surround the exposed portion of the conductive element.

In some examples, the barrier may further comprise a base wall which extends radially from the annular wall toward the conductive element. In this example, the barrier is in the form of a cup. The base preferably closes the barrier at a proximal end or side of the barrier, i.e. it closes the cup at the base.

In accordance with one or more embodiments, the radial spacing between the annular wall and the conductive element may be non-uniform.

By way of one example, the barrier may be a frustoconical element, with the annular wall arranged tapering radially outward from the conductive element in the direction of a distal end of the conductive element. A distal face of the barrier may be open. The wall in this case is angled away from the conductive element.

In accordance with one or more embodiments, each electrode may comprise an electrically insulating sheath having a first section in solid contact with the conductive element along a first length portion of the conductive element, the first length portion of the conductive element forming a non-exposed portion of the conductive element.

At least one wall of the barrier may be formed by a second section of the sheath, extending from a distal end of the first section, the second section being radially spaced from a second length portion of the conductive element, the second length portion forming the exposed portion of the conductive element. Thus, the barrier is formed by a distal portion of an insulating sheath which covers a proximal portion of the conductive element. This provides a structurally efficient configuration.

In some examples, the second section of the insulating sheath may taper radially outward from the conducting element, from the distal end of the first section of the sheath.

In accordance with one or more embodiments, the barrier may extend to a maximal width which is greater than a maximal width of the electrode (without the barrier). This has the effect that the barrier forces a physical separation between any two electrodes, at least between the sections of the electrodes covered by the barrier element. The barrier element acts to deflect physical contact. In other words, the barrier element forms an extended width portion of the electrode.

Further examples of the invention provide an oral care device comprising: an oral cleaning and/or treatment unit in accordance with any example or embodiment outlined above or described below, or in accordance with any claim of this application; and a signal generator adapted to generate one or more drive signals for supply to the plurality of electrodes of the oral cleaning and/or treatment unit, e.g. for stimulating generation of radio frequency (RF) electromagnetic emissions or currents from the electrodes.

In the context of this disclosure, 'emissions' may refer to a static or time-varying electric or electromagnetic field, and/or to propagating electromagnetic waves.

The oral care device may further comprise a mechanical movement generator arranged to apply an oscillatory movement to the support body of the cleaning and/or treatment unit.

Oscillatory movement of the electrodes can increase the chance of contact between electrodes. Thus, the barrier is of particular utility for such embodiments.

According to one or more embodiments, the oral care device may be a toothbrush or a mouthpiece device.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 7 illustrates an example cleaning and/or treatment unit according to one or more embodiments comprising a plurality of cleaning elements surrounding the pair of electrodes;

FIG. 8 illustrates bending of the electrodes of the example cleaning and/or treatment unit of FIG. 7 toward one another, and the shielding action of the barrier;

FIG. 9 illustrates in plan view a layout of an example set of spatial groups of cleaning elements, with electrodes nestled inside a selection of the spatial groups;

DETAILED DESCRIPTION OF THE EMBODIMENTS

Figures 1, 2, 3, 4:
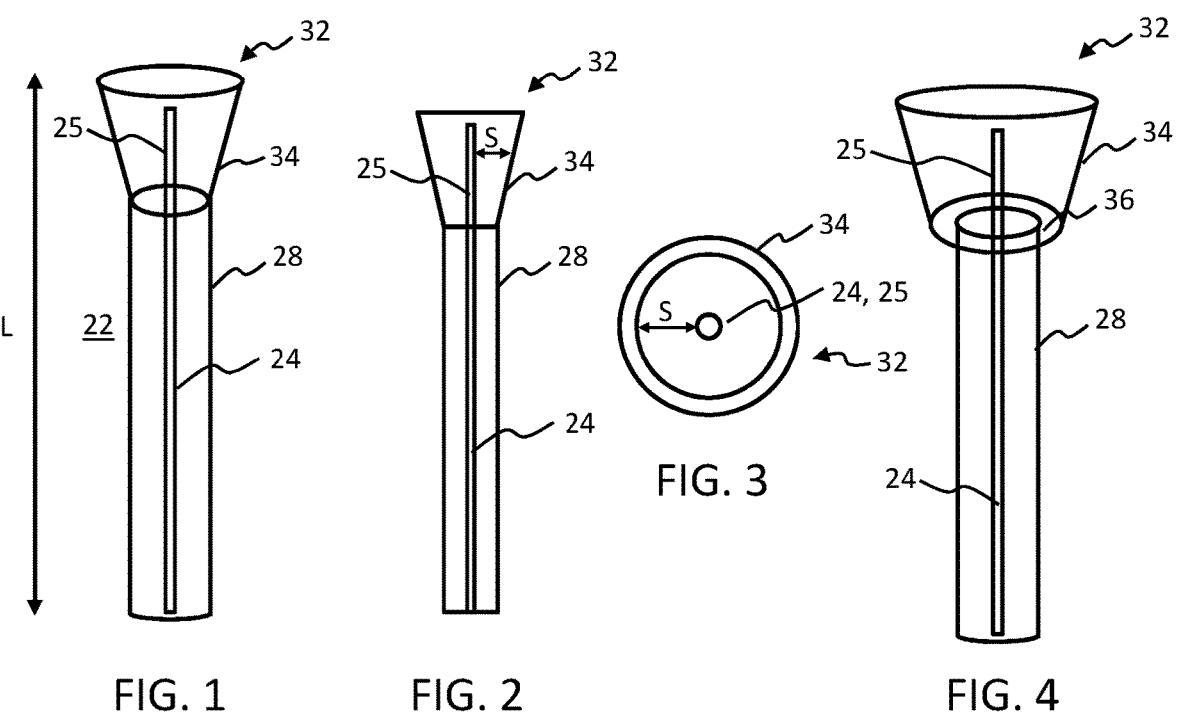
FIG. 1 shows a perspective view of an example electrode comprising a barrier, in accordance with one or more embodiments.
FIG. 2 shows an elevation view of the example electrode depicted in FIG. 1.
FIG. 3 shows a plan view of the example electrode depicted in FIGS. 1-2.
FIG. 4 shows a perspective view of an electrode comprising a further example barrier according to one or more embodiments.

The invention will be described with reference to the Figures.

It should be understood that the detailed description and specific examples, while indicating exemplary embodiments of the oral cleaning and/or treatment unit and the oral care device, are intended for purposes of illustration only and are not intended to limit the scope of the invention. These and other features, aspects, and advantages of the oral cleaning and/or treatment unit and the oral care device of the present invention will become better understood from the following description, appended claims, and accompanying drawings. The Figures are merely schematic and are not drawn to scale. The same reference numerals are used throughout the Figures to indicate the same or similar parts.

The invention provides a physical shielding element carried by EM emitter elements of a cleaning and/or treatment unit for an oral care device, arranged for interposing contact of an exposed conductive portion of the emitter element by other components or external objects. The shielding element is arranged such that the exposed conductive portion is still at least partially open to the environment surrounding the emitter element.

FIGS. 1-3 show an example electrode 22 of an oral cleaning and/or treatment unit 12 in accordance with one or more embodiments. FIG. 1 shows a perspective view. FIG. 2 shows an elevation view. FIG. 3 shows plan (top-down) view.

When assembled, the electrode 22 would be arranged extending outwardly from a surface of a support body 14 of the cleaning and/or treatment unit 12. It would preferably be provided as one of a plurality of electrodes 22. A plurality of pairs of electrodes 22 may be provided.

The electrode 22 comprises a conductive element 24 which runs axially through a core of the electrode structure. A distal portion 25 of the conductive element 24 is exposed, by which is meant that this portion of the conductive element 24 is open to, or in direction fluid communication with, the environment surrounding the cleaning and/or treatment unit 12, for example open to the air. The electrode 22 is preferably flexible in a lateral direction, by which is meant it is bendable in a direction transverse a dimension defined by its length L.

There is further provided a barrier 32, carried by the electrode. The barrier 32 in this example is in the form of a physical barrier element. The barrier 32 comprises one or more walls 34 spaced from the exposed portion 25 of the conductive element 24. The walls are arranged to at least partially shield the exposed portion 25 against physical contact. The barrier 32 is optionally electrically insulating.

In this example, the exposed portion 25 of the conductive element forms a distal tip portion, extending to a terminal distal point of the conductive element 24.

In the illustrated example, the barrier 32 comprises an annular wall 34 which annularly surrounds the exposed portion 25 of the conductive element 24. There is a radial spacing S between the annular wall 34 and the exposed portion 25 of the conductive element 24. The spacing S for example forms an air gap. The annular wall is arranged facing opposite at least a portion of an outer surface of the exposed portion 25 of the conductive element 24, and spaced from the outer surface of the exposed portion 25. The annular wall 34 may co-axially surround the exposed portion 25 of the conductive element 24.

Although in the example of FIG. 1, the annular wall 34 forms a continuous annular loop around the exposed portion 25 of the conductive element 24, this is not essential. The annular wall 34 may be discontinuous, with one or more breaks in some examples.

Furthermore, although the barrier 32 has an annular wall 34 in the example of FIG. 1, this is not essential. For example, in variations, the conductive element 25 may have a flat or planar form, with planar major surfaces on reverse sides of the conductive element 25, and wherein the barrier 32 comprises a pair of walls arranged facing opposite to each of the planar major surfaces. The walls may be planar.

The one or more walls 34 are arranged to form a physical shield against physical contact of the exposed portion 25 of the conductive element 24 by other electrodes 22, or by other external bodies approaching from a direction on the reverse sides of the walls 34. The walls 34 interpose contact by bodies approaching from the sides of the electrode.

In the illustrated example, the radial spacing S between the annular wall 34 and the conductive element 24 is non-uniform. In particular, the annular wall 34 tapers radially outward along its length. It tapers from a proximal end, with a first diameter, to a distal end with a second, larger diameter. The distal end is open. The proximal end is coupled to a distal end of an electrically insulating cover or sheath 28 which covers a stem section of the conductive element 24, the stem section not being exposed.

The barrier 32 consequently defines a frustoconical shape. A width of the wall 34 in this example is uniform, but this is not essential. The barrier effectively follows a funnel shape.

FIG. 4 shows a further example in which the barrier 32 takes the form of cup shape. In particular, the barrier 32 further comprises a base wall 36 which extends radially from the annular wall 34 toward the conductive element. In the illustrated example, it extends (substantially) laterally from a proximal edge or rim of the annular wall 34 to a distal edge or rim of an insulative sheath 28 which covers the stem portion of the conductive element 24. The base wall 36 thus closes the barrier 32 at its base. The barrier 32 remains open at its distal face.

As a consequence of the barrier 32, the exposed portion 25 of the conductive element 24 is partially physically protected from contact by elements approaching from directions transverse the electrode 22, while still allowing the distal portion of the conductive element 24 to be exposed, allowing for efficient output of EM energy from the electrode 22 and/or for currents to flow. The barrier 32 reduces the possibility of contact of the exposed portion 25 by a neighboring electrode on the surface of the oral cleaning and/or treatment unit, thereby reducing the chance of short circuiting.

As mentioned, the barrier 32 may be formed of a non-conductive material and may form a dielectric barrier around the exposed portion 25 of the conductive element 24, to prevent short circuiting. The open shape of the barrier 32, and its spacing from the conductive element still allows the RF field to be generated at the tip, which, in use, advantageously forms the closest point to the target surface (teeth & gums). By way of non-limiting example, the barrier 32 may be formed of a dielectric elastomer material, such as rubber.

In some embodiments, the one or more walls 34 of the barrier 32 may comprise small holes which permit ion flow, while still preventing mechanical contact between the electrodes 22. The barrier 32 hence has a structure analogous to a filter membrane. The size of the holes may fall anywhere within a range of sizes, the lower bound of which is constrained by the need for the ions to be able to pass, and the upper bound of which is constrained by the need to maintain structural integrity of the barrier 32. By way of example, a suitable range may be between 10 nm and 50 μm (diameter).

As mentioned above, preferably each of the electrodes 22 is flexible. In some advantageous examples, at least a subset of the electrodes 22 may be adapted to double as cleaning filaments. Thus, at least a subset of the electrodes 22 may be adapted for performing a mechanical cleaning function in addition to the RF emission function. This arrangement may be preferred since no compromise needs to be made between mechanical brushing efficacy and RF field output efficacy. The presence of the electrodes 22 does not take away available space on the cleaning and/or treatment unit surface 12 for presence of mechanical cleaning elements (e.g. bristles).

The barrier 32 according to embodiments of the present invention is particularly advantageous in such cases since the flexible electrodes 22 have greater likelihood of bending and potentially contacting one another, leading to short-circuits.

Thus, the barrier 32 carried by each electrode 22 may preferably be arranged to interpose contact of the exposed portions 25 of the electrode 22 conductive elements 24 of each pair of neighboring electrodes 22 upon bending of the electrodes 22 toward one another.

Although in the above examples, the annular wall 34 of the barrier 32 is angled or inclined relative to the (length of the) electrode 22 (i.e. tapered), this is not essential. The wall(s) 34 may extend parallel to a length dimension of the electrode 22.

Although in the examples outlined above, the whole of the wall 34 of the barrier 32 is spaced by an air gap from the exposed portion of the conductive element 24, this is not essential. In further examples, a part or the whole of the barrier 32 may be in contact with the conductive element 24. For example, the barrier 32 may comprise an annular wall 34 which surrounds the conductive element 24, and with a filling between the annular wall 34 and the conductive element 24. The filling may be dielectric filling. Instead of a wall 34 with a dielectric filling, the barrier 32 may be a unitary (monolithic) solid structure, for example formed of a single material, shaped to prevent the exposed portion 25 of one electrode 22 from being physical contacted by another electrode 22. The exposed portion of the conductive element may protrude from a top of the barrier 32 in these cases.

Figures 5, 6:
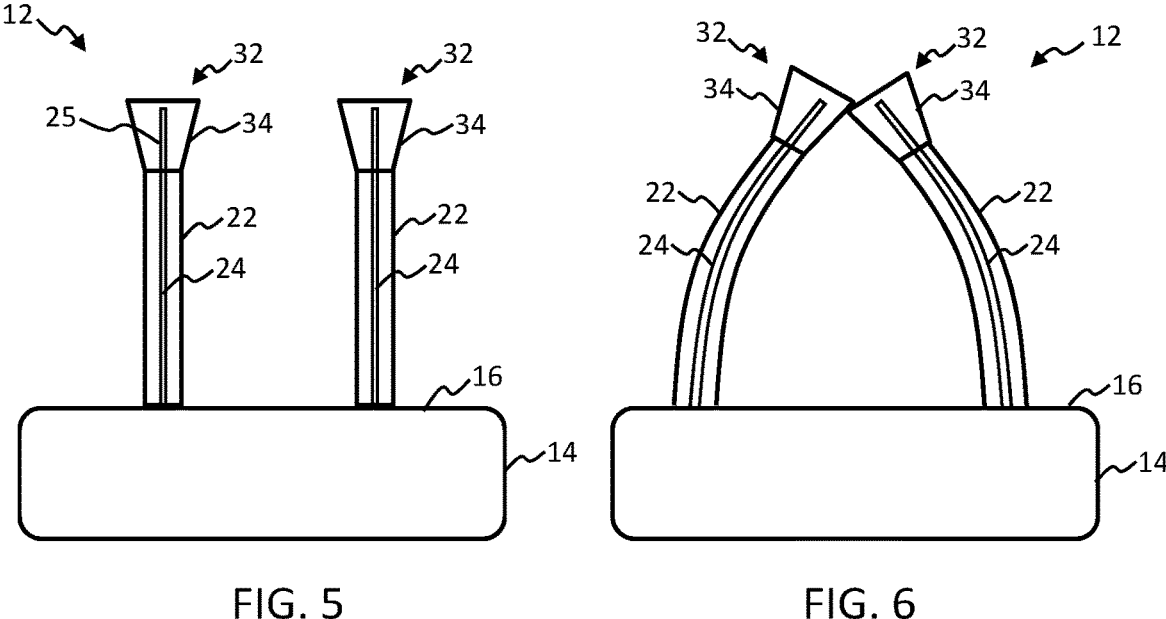
FIG. 5 shows an example cleaning and/or treatment unit according to one or more embodiments, carrying a pair of electrodes, each carrying a barrier.
FIG. 6 illustrates bending of the electrodes of the cleaning and/or treatment unit of FIG. 5 toward one another, and the shielding action of the barrier.

By way of one example, the barrier 32 may comprise a frustoconical or cup-shaped element, as in the examples of FIG. 1 and FIG. 5, but wherein the barrier 32 is solidly filled between the conductive element 24 and the wall 34, and wherein the conductive element 24 protrudes from a distal end of the barrier 32, the protrusion forming the exposed portion 25 of the conductive element 24. In this case, the barrier 32 still provides protection of the exposed portion 25 of the conductive element 24, since its extended maximum width compared with the lower part of the electrode 22 (proximal of the barrier element) acts to deflect physical contact, or to force a greater physical separation between distal regions of nearby electrodes.

Preferably, the barrier 32 in all cases is not a coating, where a coating has the meaning normally used in the art, i.e. a thin, usually uniform-thickness skin or covering of the conductive element.

FIGS. 5 and 6 schematically illustrate an example cleaning and/or treatment unit 12 for an oral care device in accordance with one or more embodiments of the invention. The cleaning and/or treatment unit 12 comprises a support body 14, and a plurality of electrodes 22 outwardly extending from a surface 16 of the support body 14. Although only two electrodes 22 are shown in FIG. 5 and FIG. 6, more than two may be provided. The plurality of electrodes 22 may comprise one or more pairs of electrodes 22. In operation, the electrodes 22 of a given pair may be driven with differing voltages so that there is a potential difference between them. Therefore, contact between the electrodes 22 can lead to generation of heat through short-circuiting.

FIG. 5 shows an example cleaning and/or treatment unit 12 in a state of low wear or degradation of the electrodes 22 (e.g. a factory-new state), in which the electrodes 22 are straight, and are not bent toward one another. It may alternatively represent a rest state of the unit, when the electrodes 22 are not being deflected by contact with surfaces in the mouth.

FIG. 6 shows the example cleaning and/or treatment unit 12 in a state of higher wear or degradation, in which the electrodes 22 are bowed or deformed, so that they bend toward one another, or have lost their structural rigidity to resist being bent toward one another during use. Alternatively, it may represent a state of low wear, but wherein the electrodes 22 are being bent toward one another during use of the unit in the mouth, leading to exertion of forces on the electrodes 22. In either case, in prior art devices, this would risk a short circuit due to contact between exposed portions 25 of the conductive elements 24 of the electrodes 22. As illustrated in FIG. 6, the barrier 32 carried by each of the electrodes 22 in accordance with embodiments of this invention are in the form of physical barrier elements arranged to block contact of the exposed portion of each electrode's conductive element 24 by the other electrode 22 (due to relative bending of the electrode(s) 22 toward one another).

Although in FIG. 5 and FIG. 6 both electrodes of the illustrated pair of electrodes 22 comprises a barrier 32, this is not essential. More generally, only one of the pair of electrodes 22 may comprise a barrier 32, since this by itself guards against physical contact between the exposed conductive portions 25 of the two electrodes of the pair. More generally, only a subset of one or more of the plurality of electrodes 22 comprised by the cleaning and/or treatment unit 12 is required to comprise a physical barrier element.

As discussed above, the cleaning and/or treatment unit 12 may further comprise a plurality of mechanical cleaning elements 52 outwardly extending from the surface of the support body 14 for mechanically engaging with surfaces in an oral cavity of a user for a cleaning function. The cleaning elements may for example comprise cleaning filaments such as bristles, and/or may comprise bundles of cleaning filaments such as bristles. The electrodes 22 may each be nestled amongst a field of cleaning elements.

FIGS. 7-8 schematically illustrate an example cleaning and/or treatment unit 12 comprising a plurality of cleaning elements 52 and a plurality of electrodes 22 in accordance with one or more embodiments of the invention. The electrodes 22 may be arranged such that they are surrounded by cleaning elements 52 or bundles of cleaning elements 52.

For example, the plurality of cleaning elements 52 may comprise at least one spatial group of cleaning elements 52, the spatial group covering an area of the support body 14 surface 16, and wherein the at least a subset of the plurality of electrodes 22 outwardly extends from locations on the support body surface 16 within the area. The spatial group may form a tuft of cleaning elements 52 or a field of cleaning elements 52, where the field may comprise a plurality of tufts, or a plurality of individual cleaning filaments.

The electrodes 22 are preferably flexible in a lateral direction, by which is meant bendable in a direction transverse a dimension defined by its length, L.

The at least subset of the plurality of electrodes 22 may extend to the same height (from the surface 16 of the cleaning and/or treatment unit 14) as the cleaning elements 52. The distal tips of cleaning elements 52 of the spatial group of cleaning elements may define a height profile which may or may not be a uniform height from the surface 16, and wherein the distal tips of the electrodes lie within the height profile.

One or more pairs of electrodes 22, driven with differing drive voltages, may be located within the same spatial group of cleaning elements 52. This makes short-circuiting more likely, which makes the barrier 32 of particular utility in this circumstance.

FIG. 8 illustrates for example a state of mechanical wear or degradation of the cleaning and/or treatment unit 12, in which the electrodes 22 and bristles 52 are partially deformed and bent, or have lost their flexural rigidity, such that they are more liable to bending. Alternatively, it may represent the unit in operation in the mouth, in which the electrodes 22 are being deflected due to contact with surfaces in the mouth or due to oscillation by a mechanical oscillator. As shown, the distal portions of the electrodes 22 may have greater risk of contacting one another, particularly if located in the same field (or other spatial group) of cleaning elements 52. The barrier 32 according to embodiments of the present invention interpose contact between at least the exposed portions 25 of the electrode conductive elements 24, thereby preventing short circuits.

FIG. 9 further schematically illustrates an example spatial configuration (in plan view) of the electrodes 22 and the cleaning elements 52. As illustrated, the cleaning and/or treatment unit may comprise a plurality of spatial groups 62 of cleaning elements 52. In FIG. 9, these are illustrated in the form of tufts of cleaning elements 52. One subset 62a of the spatial groups of cleaning elements 52 comprise electrodes 22 nestled among the cleaning elements 52 of the group (located extending from a point on the cleaning and/or treatment unit surface 16 which is inside the footprint area of the spatial group). Providing multiple electrodes 22 in the same spatial group (e.g. tuft) of cleaning elements is functionally advantageous since it allows for delivery of greater electromagnetic (EM) energy per unit area. Each of the first subset 62a of spatial groups of cleaning elements may comprise at least one pair of electrodes 22 which, in operation, are driven with differing voltages.

A further subset 62b of the spatial groups of cleaning elements 52 comprises no electrodes 22. However, this is not essential and in further embodiments, all spatial groups of cleaning elements 52 may comprise one or more electrodes 22. As can be seen, when a plurality of electrodes 22 is included within the same spatial group (e.g. tuft or field) of cleaning elements 52, the likelihood of contact between electrodes 22 is high. The tuft is spatially confined, for example with neighboring cleaning elements 52 touching one another even when in a static, neutral state. Thus, the use of the barrier 32 is particularly advantageous in such examples.

In a further set of examples, the electrodes 22 may be positioned outside of spatial groups of cleaning elements 52, for example in-between two or more spatial groups of cleaning elements 52. Preferably, in this case, the electrodes 22 may extend to a height from the surface that is less than the height of the cleaning elements 52. This avoids the electrodes 22 interfering mechanically with the action of the cleaning elements 52 in engaging with surfaces in the oral cavity.

Figures 10, 11, 12, 13:
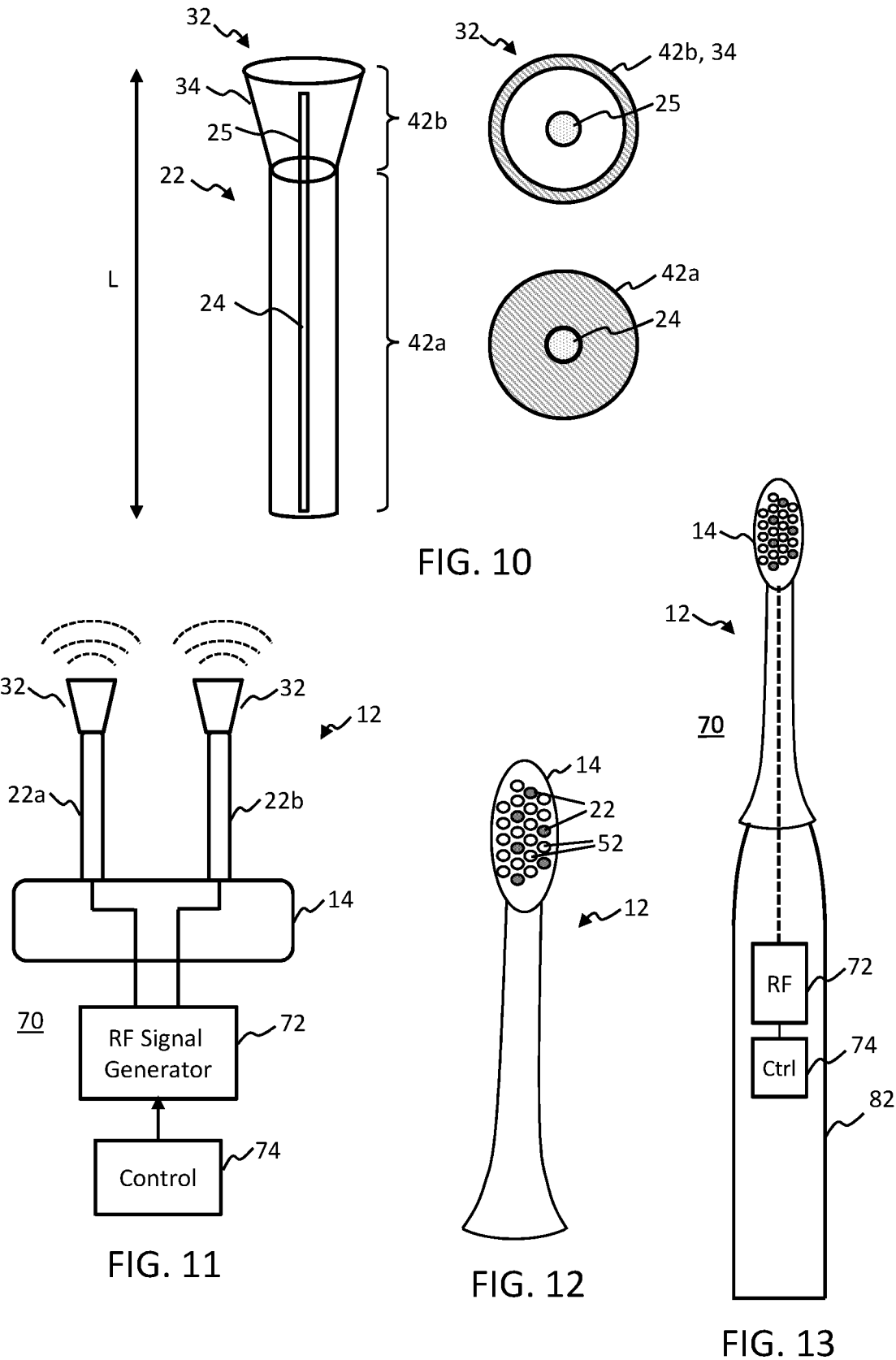
FIG. 10 shows an electrode with an example barrier formed from a distal section of an insulative sheath of the electrode.
FIG. 11 shows an example drive circuit for driving RF emission generation by electrodes of the cleaning and/or treatment unit.
FIG. 12 shows an example cleaning and/or treatment unit in the form of a toothbrush head.
FIG. 13 shows an example oral care device in the form of a toothbrush.

FIG. 10 schematically illustrates the structure of an example electrode 22 with a barrier 32 for use on a cleaning and/or treatment unit 12 in accordance with one or more embodiments. The electrode 22 comprises an electrically insulating sheath 42 having a first section 42a in solid contact with the conductive element 24 of the electrode along a first length portion of the conductive element. The first section 42a of the sheath coaxially surrounds and covers the first length portion of the conductive element 24, with the first length portion forming a core of the electrode. The first length portion of the conductive element 24 forms a non-exposed portion of the conductive element 24.

The sheath further comprises a second section 42b, extending outwardly from a distal end of the first section 42a. The second section 42b of the sheath forms the barrier 32. In particular, in the illustrated example, the second section 42b of the sheath forms an annular wall 34, radially spaced from, and annularly surrounding, a second length portion of the conductive element 24, the annular wall defining the barrier 32. The second length portion forms the exposed portion 25 of the conductive element 24.

FIG. 10 (left) shows a perspective view of the electrode 22. FIG. 10 (top right) shows a plan view of the electrode 22, in which the second section 42b of the sheath forming the barrier 32 is visible. FIG. 10 (bottom right) shows a cross-section through the electrode, across a plane perpendicular to a length, L, dimension (i.e. axial dimension) of the electrode, and through the portion of the electrode covered by the first section 42a of the sheath. As shown, the first section 42a of the sheath is in solid contact with the first length portion of the conductive element 24.

Thus, the barrier 32 in this example is formed by a distal portion 42b of an insulating sheath which also covers a proximal portion of the conductive element. This is thus a structurally efficient configuration.

The second section 42b of the insulating sheath tapers radially outward from the distal end of the first section 42a of the sheath in the direction of the distal tip of the electrode 22. In other words, it defines a frustoconical shape, with a larger diameter at an (open) distal end than at a proximal end, the proximal end being coupled to the distal end of the first section 42a of the sheath.

Examples in accordance with a further aspect of the invention provide an oral care device 70.

FIG. 11 shows the basic components of an example oral care device 70 in accordance with one or more embodiments. The oral care device 70 comprises: an oral cleaning and/or treatment unit 12 in accordance with any example or embodiment outlined above or described below, or in accordance with any claim of this application. The oral care device 70 further comprises a signal generator 72 adapted to generate one or more drive signals for supply to the plurality of electrodes 22a, 22b of the oral cleaning and/or treatment unit 12, for stimulating generation of RF electromagnetic emissions from the electrodes.

Although the example of FIG. 11 shows a single pair of electrodes 22a, 22b, more electrodes 22 may be provided in further examples, either in pairs, or as further individual electrodes.

The signal generator 72 may generate a drive signal in the form of an alternating current or voltage for supply to the electrodes 22a, 22b. The drive signal is for stimulating generation by the electrodes of a time-varying electromagnetic field and/or electromagnetic waves in the radio frequency band. By way of example a suitable frequency range may be between 30 Hz and 300 GHz.

The signal generator 72 may supply different voltages to the two electrodes 22a, 22b of the pair. It may supply opposite polarity voltages to the two. It may be arranged to supply the same drive signal to every electrode 22, or every pair of electrodes, or may be operable to supply a different drive signal to different subsets of electrodes 22, e.g. different spatial groups of electrodes comprised by the cleaning and/or treatment unit 12. The electrodes 22 are adapted to generate electromagnetic emissions upon being driven with the drive signal from the signal generator 72.

Optionally, the oral care device 70 may further comprise a controller 74 arranged to control operation of the signal generator 72. For example, it may control a drive scheme of the electrodes 22, for example controlling activation and deactivation of different spatial groups of electrodes 22 and/or controlling timing of RF emission (RF field or RF wave) generation.

In preferred embodiments, the cleaning and/or treatment unit 12 of the oral care device 70 further comprises a plurality of cleaning elements (e.g. bristles) 52.

In preferred embodiments, the oral care device further comprises a mechanical movement generator (not shown in FIG. 11) arranged to apply an oscillatory movement to the support body of the cleaning and/or treatment unit 12. This may be coupled to the controller 74. The oscillatory movement causes oscillation of the cleaning elements 52 which enhances cleaning and/or treatment action when the cleaning elements 52 are applied against oral surfaces.

The oscillatory movement also may cause movement of the electrodes 22. The oscillatory movement of the electrodes 22 can increase the chance of contact between electrodes 22. Thus, the barrier 32 is of particular utility for such embodiments.

FIGS. 12-13 shows one example oral care device 70 in the form of a toothbrush. In this example, the oral cleaning and/or treatment unit 12 is in the form of a detachable brush head for the toothbrush, and wherein the support body 14 carrying the electrodes 22 and bristle field 52 is formed by a platen portion of the brush head. The brush head in this example forms a removable attachment to a base portion 82 of the toothbrush, the base portion forming a handle for the device. The signal generator 72 and optional controller 74 are housed within the base portion 82. An oscillatory movement generator may also be provided housed in the base portion (82), and arranged to apply an oscillatory movement to the cleaning and/or treatment unit 12.

The base unit 82 and the cleaning and/or treatment unit 12 may comprise complementary electrical connectors arranged such that, upon mechanical coupling or docking of the cleaning and/or treatment unit 12 to the base unit, electrical connection is established between the signal generator 72 and the electrodes 22 comprised by the cleaning and/or treatment unit.

Although the example of FIGS. 12-13 shows an oral care device 70 in the form of a toothbrush, this is not essential. By way of further non-limiting example, the oral care device may take the form of a mouthpiece device, comprising a body defining tooth-receiving channels, and with bristles arranged protruding into the channels for a tooth cleaning function. The body may for example be U-shaped, or C-shaped, or J-shaped. Further examples include oral irrigators, powered flossing devices or any other oral care device.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

As discussed above, certain embodiments may make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Measures recited in mutually different dependent claims may advantageously be combined. If the term "adapted to" is used in the claims or description, it is noted the term "adapted to" is intended to be equivalent to the term "configured to". Any reference signs in the claims should not be construed as limiting the scope.

The invention claimed is:

1. A cleaning and/or treatment unit for an oral care device, the cleaning and/or treatment unit comprising:
   a support body; and
   a plurality of electrodes outwardly extending from a surface of the support body, the electrodes comprising a conductive element having an exposed distal portion;
   wherein the electrodes are provided with a barrier attached to the electrodes, wherein the barrier comprises a wall arranged to prevent the exposed portion from being physical contacted by another one of the plurality of electrodes,
   wherein the barrier is an annular element having an annular wall which annularly surrounds the exposed portion of the conductive element,
   wherein the radial spacing is non-uniform, and
   wherein the barrier is a frustoconical element, with the annular wall arranged tapering radially away from the conductive element in the direction of a distal end of the conductive element.

2. A cleaning and/or treatment unit as claimed in claim 1, further comprising a plurality of cleaning elements outwardly extending from the surface of the support body for use in mechanically engaging with surfaces in an oral cavity of a user for a cleaning and/or treatment function.

3. A cleaning and/or treatment unit as claimed in claim 2, wherein the plurality of cleaning elements comprises at least one spatial group of cleaning elements, the spatial group covering an area of the surface of the support body, and wherein the electrodes outwardly extend from locations on the support body surface within the area.

4. A cleaning and/or treatment unit as claimed in claim 1, wherein each of the electrodes has a length extending between a proximal end of the electrode, connected to the surface of the cleaning and/or treatment unit, and a distal end, and wherein each of the electrodes is flexible in a direction perpendicular to a direction of the length.

5. A cleaning and/or treatment unit as claimed in claim 1, wherein the barrier is arranged to interpose physical contact of the exposed portion of the conductive element by the other electrode on the surface bending toward the exposed portion.

6. A cleaning and/or treatment unit as claimed in claim 1, wherein the barrier has one or more walls radially spaced from the exposed portion of the conductive element.

7. A cleaning and/or treatment unit as claimed in claim 6, wherein the one or more walls of the barrier are each arranged facing opposite at least a portion of an outer surface of the exposed portion of the conductive element.

8. A cleaning and/or treatment unit for an oral care device, the cleaning and/or treatment unit comprising:
   a support body; and
   a plurality of electrodes outwardly extending from a surface of the support body, the electrodes comprising a conductive element having an exposed distal portion;
   wherein the electrodes are provided with a barrier attached to the electrodes, wherein the barrier comprises a wall arranged to prevent the exposed portion from being physical contacted by another one of the plurality of electrodes,
   wherein each electrode comprises an electrically insulating sheath having a first section in solid contact with the conductive element along a first length portion of the conductive element, the first length portion of the conductive element forming a non-exposed portion of the conductive element, and
   wherein at least one wall of the barrier is formed by a second section of the sheath, extending from a distal end of the first section, the second section being radially spaced from a second length portion of the conductive element, the second length portion forming the exposed portion of the conductive element.

9. A cleaning and/or treatment unit as claimed in claim 8, wherein the second section of the insulating sheath tapers radially outward from the conducting element, from the distal end of the first section of the sheath.

10. An oral care device comprising:
   a cleaning and/or treatment unit as claimed in claim 1; and
   a signal generator adapted to generate one or more drive signals for supply to the plurality of electrodes of the oral cleaning and/or treatment unit.

11. An oral care device as claimed in claim 10, wherein the oral care device is a toothbrush or a mouthpiece device.

* * * * *